(12) United States Patent
Baldenius et al.

(10) Patent No.: US 7,781,192 B2
(45) Date of Patent: *Aug. 24, 2010

(54) METHOD FOR PRODUCING D-PANTOTHENIC ACID AND/OR A SALT THEREOF VIA PURIFICATION BY CATION EXCHANGE AS ADDITIVE FOR ANIMAL FOOD

(75) Inventors: Kai-Uwe Baldenius, Ludwigshafen (DE); Christine Beck, Mannheim (DE); Hans-Peter Harz, Dudenhofen (DE); Markus Lohscheidt, Mannheim (DE); Daniela Klein, Mannheim (DE)

(73) Assignee: BASF SE, Ludwigshafen (DE)

( * ) Notice: Subject to any disclaimer, the term of this patent is extended or adjusted under 35 U.S.C. 154(b) by 947 days.

This patent is subject to a terminal disclaimer.

(21) Appl. No.: 10/468,609

(22) PCT Filed: Feb. 20, 2002

(86) PCT No.: PCT/EP02/01753

§ 371 (c)(1),
(2), (4) Date: Aug. 21, 2003

(87) PCT Pub. No.: WO02/066663

PCT Pub. Date: Aug. 29, 2002

(65) Prior Publication Data

US 2004/0048344 A1 Mar. 11, 2004

(30) Foreign Application Priority Data

Feb. 21, 2001 (DE) .................................. 101 08 225

(51) Int. Cl.
*C12P 13/04* (2006.01)
*C12P 21/02* (2006.01)
*B01D 15/04* (2006.01)
*B01J 39/00* (2006.01)
*C07C 229/08* (2006.01)

(52) U.S. Cl. ...................... 435/106; 435/69.1; 210/660; 562/569

(58) Field of Classification Search ................. 435/106, 435/116, 69.1, 224; 423/157; 210/660; 562/569
See application file for complete search history.

(56) References Cited

U.S. PATENT DOCUMENTS

| 5,518,906 A | * | 5/1996 | Hikichi et al. ............... 435/116 |
| 5,952,206 A | | 9/1999 | Giselbrecht et al. |
| 6,171,845 B1 | | 1/2001 | Elischweski et al. ... 425/252.33 |
| 6,582,939 B1 | * | 6/2003 | Binder et al. ............... 435/106 |
| 2004/0050335 A1 | * | 3/2004 | Muller et al. ............ 119/51.01 |
| 2007/0202571 A1 | | 8/2007 | Eikmanns et al. |

FOREIGN PATENT DOCUMENTS

| DE | 40 25 962 | 2/1992 |
| EP | 0 493 060 | 7/1992 |
| EP | 493 060 | 7/1992 |
| EP | 0 590 857 | 4/1994 |
| EP | 590 857 | 4/1994 |
| EP | 1 001 027 | 5/2000 |
| EP | 1 006 192 A2 | 6/2000 |
| EP | 2 006 192 | 6/2000 |
| EP | 1 050 219 | 11/2000 |
| GB | 562 267 | 6/1944 |
| WO | WO 97/10340 | 3/1997 |
| WO | 01/21772 | 3/2001 |
| WO | 02/24001 | 3/2002 |
| WO | 02/066666 | 8/2002 |

OTHER PUBLICATIONS

CRC Handbook of Chemistry and Physics, 51st Ed., R.C. Weast, ed., The Chemical Rubber Co., Cleveland, 1970, p. B-77, Physical Constants of Inorganic Compounds, entry for calcium hydroxide.*
Baigori et al., "Isolation and characterization of *Bacillus subtilis* mutants blocked in the synthesis of pantothenic acid," J Bacteriology 173(13):4240-4242, 1991.*
Sorokin et al., "Sequence analysis of the *Bacillus subtilis* chromosome region between the serA and kdg loci cloned in a yeast artificial chromosome," Microbiol 142:2005-2016, 1996.*
Federal Register 70(7):1818-1824, Jan. 11, 2005.*
Begley et al., The Biosynthesis of Coenzyme A in Bacteria, Vitamins and Hornones, Feb. 2001, pp. 157-171, vol. 61, Conrnell University.
Henner et al., *Bacillus subtills* (clone YAC15-6B) ypiABF genes, qcrABC gnes, ypJABCDEFGHI genes, birA gene, panBCD genes, dinG gene, ypmB gene, aspB gene . . . EMBL Record No. L4770g.1, BSYPIA, Jan. 23, 1996.

* cited by examiner

*Primary Examiner*—Karen Cochrane Carlson
*Assistant Examiner*—Rosanne Kosson
(74) *Attorney, Agent, or Firm*—Novak Druce + Quigg LLP

(57) ABSTRACT

The invention relates to an improved method for producing D-pantothenic acid and/or the salts thereof and the use of said substance as an additive for animal food.

16 Claims, No Drawings

METHOD FOR PRODUCING D-PANTOTHENIC ACID AND/OR A SALT THEREOF VIA PURIFICATION BY CATION EXCHANGE AS ADDITIVE FOR ANIMAL FOOD

CROSS REFERENCE TO RELATED APPLICATIONS

The instant application is a U.S. National Stage Application of International Application Number PCT/EP02/01753, filed Feb. 20, 2002.

NAMES OF PARTIES TO A JOINT RESEARCH AGREEMENT

Subject matter described and claimed in the instant patent was developed pursuant to a joint research agreement between Omnigene Bioproducts, Inc. and BASF Aktiengesellschaft.

TECHNICAL FIELD

The present invention relates to an improved process for preparing D-pantothenic acid and/or salts thereof and to the use thereof as additive to animal feedstuffs.

BACKGROUND ART

As a starting material of the biosynthesis of coenzyme A, D-pantothenate is widely distributed in the plant and animal kingdoms. In contrast to humans who consume sufficient quantities of pantothenic acid via the diet, symptoms of D-pantothenate deficiency are frequently described not only for plants but also for animals. The availability of D-pantothenate is therefore of great economic interest, particularly in the animal feed industry.

Conventionally, D-pantothenate is prepared by chemical synthesis from D-pantolactone and calcium β-alaninate (Ullmann's Encyclopedia of Industrial Chemistry, $6^{th}$ edition, 1999, electronic release, chapter "Vitamins"). The preparation of D-pantolactone requires complex, classical racemate cleavage via diastereomeric salts. The commercial product resulting from the chemical synthesis is usually the calcium salt of D-pantothenic acid, calcium D-pantothenate.

Compared with chemical synthesis, the advantage of biotechnological production processes using microorganisms is the selective (enantiomerically pure) production of the D form of pantothenic acid, which can be used for higher organisms. A complex racemate cleavage, as required in chemical synthesis, is thus not necessary.

Numerous fermentation processes for preparing D-pantothenic acid using microorganisms are known, including in EP-0 590 857, WO 96/33283, U.S. Pat. No. 6,013,492, WO 97/10340, DE 198 46 499, EP 1 001 027, EP 1 006 189, EP 1 006 192 and EP 1 006 193.

Thus EP 1 006 189 and EP 1 001 027 describe processes for preparing pantothenate in which a content of at most 1 g/l of D-pantothenic acid in the fermentation solution is achieved. Such low pantothenic acid contents in the fermentation solution, that is to say of less than 10% by weight, based on the solids content, are unsuitable, however, for economic preparation of D-pantothenic acid-containing animal feed supplements. A further disadvantage with the processes described to date is that isolating the product from the fermentation medium requires numerous complex work-up steps. An economic preparation process on the industrial scale is not known.

German Laid Open Application DE 100 16 321 describes a fermentation process for preparing a D-pantothenic acid-containing animal feed supplement. However, an important disadvantage of this process, as with the above-described fermentation processes for preparing D-pantothenic acid, is that the pantothenic acid precursor β-alanine must be supplied to the microorganism via the fermentation medium in order to obtain economic yields of the desired product.

In addition, U.S. Pat. No. 6,013,492 and WO 96/332839 describe working up the D-pantothenic acid from the fermentation solution by filtering off insoluble constituents (for example cell material) from the culture medium, adsorbing the filtrate to activated carbon, subsequently eluting the D-pantothenic acid with an organic solvent, preferably methanol, neutralizing with calcium hydroxide and subsequently crystallizing calcium D-pantothenate. Important disadvantages are the losses of valuable product occurring during crystallization and the use of an organic solvent which can only be removed with difficulty from the product and requires a complex solvent recovery step.

EP 0 590 857 describes a fermentation process for preparing D-pantothenic acid in which culturing a microorganism requires the feeding of β-alanine. The fermentation solution is filtered to separate off the biomass, then passed through a cation exchanger and then an anion exchanger, following this neutralizing with calcium hydroxide, concentrating by evaporation, adding activated carbon, filtering once more and crystallizing with addition of methanol and calcium chloride. The resultant calcium pantothenate-containing product, in addition to D-pantothenic acid in the form of the calcium salt, also contains calcium chloride in a molar ratio of 1:1. Decreasing the calcium chloride content requires electrodialysis with subsequent spray drying. This process has the disadvantage of being neither economical or ecological because of the multiplicity of complex process steps and the use of organic solvents.

SUMMARY OF THE INVENTION

It is an object of the present invention to provide an animal feed supplement containing D-pantothenic acid and/or salts thereof and its preparation by an improved process for preparing D-pantothenic acid and/or salts thereof which does not have the abovementioned disadvantages. For economic reasons, a process is desirable here in which supplying β-alanine is greatly decreased or is not required at all. In addition, preparing D-pantothenic acid in the form of its divalent salts and, especially, the alkaline earth metal salts, is desirable, since the divalent salts have less hygroscopic characteristics than monovalent salts of pantothenic acid and thus have a less pronounced trend to aggregation for further application, for example as animal feed supplement. We have found that this object is achieved advantageously by the present invention.

DETAILED DESCRIPTION OF THE INVENTION

The present invention relates to a process for preparing D-pantothenic acid and/or salts thereof which comprises a) using at least one organism which produces D-pantothenic acid and in which the biosynthesis of pantothenic acid (pan) and/or isoleucine/valine (ilv) is deregulated and which forms at least 2 g/l of salts of D-pantothenic acid by fermentation in a culture medium, 0-20 g/l of free β-alanine and/or β-alanine salt being supplied to the culture medium, b) passing the D-pantothenate-containing fermentation solution through a cation exchanger, free D-pantothenic acid being formed from the salts of D-pantothenic acid, c) adding calcium base and/or magnesium base to set the free D-pantothenic acid-containing solution to a pH of 3-10, a solution being obtained which contains calcium and/or magnesium pantothenic acid and d) subjecting the calcium pantothenate- and/or magnesium pantothenate-containing solution to drying and/or formulation.

In a variant of the inventive process, in step c), a suspension can also be obtained which contains calcium and/or magnesium chloride. In the following step d), this suspension is then subjected to drying and/or formulation.

The fermentation in step a) of the inventive process are carried out using procedures which are known per se in the batch, Fed-batch or repeated fed-batch mode or continuously. The resultant pantothenic acid is neutralized in this case using conventional buffer systems, for example phosphate buffer containing NaOH, KOH or ammonia.

In other variants of the inventive process, in step a) at least 10 g/l, preferably at least 20 g/l, particularly preferably at least 40 g/l, very particularly preferably at least 60 g/l, and in particular at least 70 g/l, of salts of D-pantothenic acid are formed in the culture medium by fermentation.

For the purposes of the present invention, the form of words "producing" means that the organism can synthesize larger amounts of D-pentothenic acid and/or salts thereof than are required for its own metabolic needs. In an inventively advantageous variant, the amount of D-pantothenic acid and/or salts thereof synthesized is not present in the interior of the cell, but ideally is completely released into the culture medium by the organism. This discharge can be active or passive by means of mechanisms which are known per se.

According to the invention the D-pantothenic acid-producing organisms used are microorganisms. These include according to the invention fungi, yeasts and/or bacteria. According to the invention, preference is given to using fungi, for example mucor, or yeasts, for example *Saccharomyces* or *Debaromyces*, and of these, preferably, *Saccharomyces cerevisiae*. Advantageously, coryneform bacteria or Bacillaceae are used according to the invention. Those which are within the scope of the invention are preferably, for example, bacteria of the genera *Corynebacterium, Escherichia, Bacillus, Arthrobacter, Bevibacterium, Pseudomonas, Salmonella, Klebsiella, Proteus, Acinetobacter* or *Rhizobium*. Particular preference is given here, for example, to *Corynebacterium glutamicum, Brevibacterium breve* or *Bacillus subtilis, B. licheniformis, B. amyloliquefaciens, B. cereus, B. lentimorbus, B. lentus, B. firmus, B. pantothenticus, B. circulans, B. coagulans, B. megaterium, B. pumilus, B. thuringiensis, B. brevis, B. stearothermophilus* and other *Bacillus* species of group 1 which are characterized by their 16sRNA, or Actinum mycetalis. This listing serves for explanation and is in no way limiting for the present invention.

Furthermore, the present invention also comprises the use of genetically modified organisms for the inventive preparation of an animal feed supplement containing free D-pantothenic acid and/or salts thereof. Such genetically modified organisms can be isolated, for example, by chemical mutagenesis and subsequent selection using a suitable "screening process". According to the invention, what are termed "production strains" are also included which are suitable for preparing the product in the meaning of the present invention and have genetic modifications with respect to the metabolic flux in the direction of D-pantothenic acid, modifications with respect to the discharge of D-pantothenic acid and/or salts thereof via the cell membrane also being included. This can be achieved, for example, by modifications at key positions in relevant metabolic biosynthesis pathways of the organism used.

It is also conceivable to use transgenic organisms which result from the transfer of homologous and/or heterologous nucleotide sequences which are necessary, or can be required, for synthesizing the desired product. In this case, overexpression and/or deregulation of one or more genes individually and/or in combination localized in the genome and/or on a vector are conceivable.

Transgenic organisms of this type can, advantageously, contain additional copies and/or genetically modified genes selected from the group consisting of panB, panC, panD, panE and/or combinations thereof and/or even organization units how contain the panBCD operon. In addition, other metabolic pathways, for example the isoleucine-valine biosynthesis pathway can be advantageously manipulated in the organisms, as is described, for example, in EP 1 006 189, EP 1 006 192, EP 1 006 193 or EP 1 001 027. As a result, branched-chain precursor substances of pantothenic acid biosynthesis are increasingly being made available. Advantageously, if appropriate, the genes for this biosynthesis pathway, i.e. ilvB, ilvN, ilvC and/or ilvD are overexpressed.

In addition, genetic modifications of aspartate α-decarboxylase (panD), for example through overexpression and/or deregulation, in the D-pantothenic acid-producing organism used are covered by the invention.

The word "deregulation", for the purposes of the present invention, means changing or modifying at least one gene which codes for one enzyme in a biosynthetic metabolic pathway, so that the activity of the enzyme is changed or modified in the microorganism. It is preferred that at least one gene which codes for one enzyme of a biosynthetic metabolic pathway is changed in such a manner that the gene product is formed to an increased extent, or has an increased activity. The term "deregulated metabolic pathway" also includes a biosynthetic metabolic pathway in which more than one gene, which codes more than one enzyme, is changed or modified in such a manner that the activities of more than one enzyme are changed or modified.

Changes or modifications can include, but are not restricted to: removing the endogenous promoter or regulatory elements; introducing strong promoters, inducible promoters or a plurality of promoters simultaneously; removing regulatory sequences, so that expression of the gene product is changed; changing the chromosomal position of the gene; changing the DNA sequence in the vicinity of the gene or within the gene, for example the ribosomal binding site (RBS); increasing the number of copies of the gene in the genome or by introducing a varying number of copies of plasmids; modifying proteins (e.g. regulatory proteins, suppressors, enhancers, transcriptional activators and the like), which play a role in the transcription of the gene and/or in the translation to give the gene product. This also includes all other possibilities for deregulating the expression of genes which belong to the prior art, for example the use of antisense oligonucleotides, or the blocking of repressor proteins.

Deregulation can also comprise changes to the coding region of genes which lead, for example, to removing feedback regulation in the gene product or to a greater or lesser specific activity of the gene product.

Furthermore, genetic modifications to enzymes are advantageous according to the invention which affect the efflux of precursors of pantothenic acid and/or the flux of pantothenic acid to give coenzyme A. Examples of genes coding for such enzymes are: alsD, avtA, ilvE, ansB, coaA, coax, etc. This listing serves for explanation and is in no way limiting for the present invention.

In addition, genetic modifications are advantageous which secure the cellular production of cofactors (e.g of methylene tetrahydrofolate, redox equivalents and the like) in an amount which is optimum for pantothenic acid production.

Advantageously, thus, β-alanine is already present in the cells in increased concentrations compared with correspondingly non-genetically modified organisms, and thus need not be added to the culture medium as precursor, as is required, for example, in EP-A 0 590 857. Microorganisms are advantageous in which the biosynthesis of pantothenic acid (pan) and/or isoleucine-valine (ilv) and/or asparate-α-decarboxylase (panD) is deregulated. Furthermore, additional overexpression of ketopanthoate reductase (panE) in the microorganisms is advantageous.

It is additionally advantageous according to the invention if, if appropriate, the coaA gene which is required for the synthesis of coenzyme A is decreased in its activity, or is entirely switched off (for example in Bacillus species). This is because Bacillus, in addition to coaA, contains a further gene for this enzymatic function (=coax). The activity of this gene coax or the corresponding enzyme can also be changed, preferably reduced, or even deleted, provided that coaA itself still has sufficient enzyme activity, albeit reduced enzyme activity, that is to say the enzyme activity of coaA is not entirely lost. In addition to the overexpression of the various genes, genetic manipulation of the promoter regions of these genes is also advantageous provided that this manipulation leads to overexpression of the gene products.

In an embodiment of the present invention, the bacterial strains described according to the annex (PCT/US application 0025993), for example Bacillus subtilis PA 824 and/or derivatives thereof, are used. In a further embodiment, according to the invention the microorganism Bacillus subtilis PA 668, as described in the annex (U.S. Ser. No. 60/262, 995), is used in the inventive process. These strains Bacillus subtilis PA 824 and PA 668 were produced as follows:

Starting from the strain Bacillus subtilis 168 (Marburg strain ATCC 6051), which has the genotype trpC2 (Trp$^-$), the strain PY79 was produced via transduction of the Trp$^+$ marker (from the Bacillus subtilis wild type W23). Classical genetic engineering methods (as described, for example, in Harwood, C. R. and Cutting, S. M. (editors), Molecular Biological Methods for Bacillus (1990) John Wiley & Sons, Ltd., Chichester, England) introduced mutations ΔpanB and ΔpanE1 into the strain PY79.

The resultant strain was transformed using genomic DNA of Bacillus subtilis strain PA221 (genotype $P_{26}$panBCD, trpC2 (Trp$^-$)) and genomic DNA of Bacillus subtilis strain PA303 (genotype $P_{26}$panE1). The resultant strain PA327 has the genotype $P_{26}$panBCD, $P_{26}$panE1, and is a tryptophan auxotroph (Trp$^-$). Pantothenic acid titers of up to 3.0 g/l (24 h) were achieved using Bacillus subtilis strain PA327 in 10 ml cultures containing SVY medium (25 g/l Difco Veal Infusion Broth, 5 g/l Difco Yeast Extract, 5 g/l of Na glutamate, 2.7 g/l of ammonium sulfate charged into 740 ml of water, the mixture was autoclaved then 200 ml of 1 M potassium phosphate, pH 7.0 and 60 ml of 50% sterile glucose solution were added), which had been supplemented with 5 g/l of β-alanine and 5 g/l of α-ketoisovalerate.

The production of Bacillus subtilis strain PA221 (genotype $P_{26}$panBCD, trpC2 (Trp$^-$)) is described in the following section:

Classic genetic engineering methods were used to clone the panBCD Operon of Bacillus, with the aid of the sequence information of the panBCD Operon of E. coli (see Merkel et al., FEMS Microbiol. Lett., 143, 1996:247-252) starting from a Bacillus subtilis GP275 plasmid library. For the cloning, use was made of E. coli strain BM4062 (bir$^{ts}$) and the information that the Bacillus operon is close to the birA gene. The panBCD operon was introduced into a plasmid which can be replicated in E. coli. To improve the expression of the panBCD operon, strong constitutive promoters of Bacillus subtilis phages SP01 ($P_{26}$) were used, and the ribosome binding site (=RBS) before the panB gene was replaced by an artificial RBS. A DNA fragment which is immediately upstream of the native panB gene in Bacillus was ligated in front of the $P_{26}$panBCD cassette on the plasmid. This plasmid was transformed into Bacillus subtilis strain RL-1 (derivative of Bacillus subtilis 168 obtained by classical mutagenesis (Marburg strain ATCC 6051), genotype trpC2 (Trp$^-$)) and, by homologous recombination, the native panBCD operon was replaced by the $p_{26}$panBCD operon. The resultant strain is called PA221 and has the genotype $P_{26}$panBCD, trpC2 (Trp$^-$).

A pantothenic acid titer of up to 0.92 g/l (24 h) was achieved using the Bacillus subtilis strain PA221 in 10 ml cultures containing SVY medium which had been supplemented with 5 g/l of β-alanine and 5 g/l of α-ketoisovalerate.

Production of the Bacillus subtilis strain PA303 (genotype $P_{26}$panE1) is described in the following section:

Using the E. coli panE gene sequence, the Bacillus panE sequence was cloned by analogy. It was found that in B. subtilis, two homologs of the E. coli panE gene exist which were termed panE1 and panE2. Deletion analyses found that the panE1 gene is responsible for 90% of the pantothenic acid production, while deleting the panE2 gene had no significant effect on pantothenic acid production. Here also, similarly to cloning the panBCD Operon, the promoter was replaced by the strong constitutive promoter $P_{26}$ and the ribosome binding site in front of the panE1 gene was replaced by the artificial binding site. The $P_{26}$panE1 fragment was cloned into a vector which was constructed so that the $P_{26}$panE1 fragment could integrate into the original panE1 locus in the Bacillus subtilis genome. The strain resulting after transformation and homologous recombination is termed PA303 and has the genotype $P_{26}$panE1. A pantothenic acid titer of up to 1.66 g/l (24 h) was achieved using the Bacillus subtilis strain PA303 in 10 ml cultures containing SVY medium which had been supplemented with 5 g/l of β-alanine and 5 g/l of α-ketoisovalerate.

The strain was further constructed by transforming PA327 with a plasmid which contained the $P_{26}$ilvBNC Operon and the marker gene for spectinomycin. The $P_{26}$ilvBNC operon integrated into the amyE locus, which was demonstrated by PCR. One transformant was termed PA340 (genotype $P_{26}$panBCD, $P_{26}$panE1, $P_{26}$ilvBNC, specR, trpC2 (Trp$^-$)).

A pantothenic acid titer of up to 3.6 g/l (24 h) was achieved using the Bacillus subtilis strain PA340 in 10 ml cultures containing SVY medium which had been supplemented only with 5 g/l of β-alanine; in 10 ml cultures containing SVY medium which had been supplemented with 5 g/l of β-alanine and 5 g/l of α-ketoisovalerate, a pantothenic acid titer of up to 4.1 g/l (24 h) was achieved.

In addition, a deregulated ilvD cassette was introduced into strain PA340. For this, a plasmid which contains the ilvD gene under the control of the $P_{26}$ promoter containing the artificial RBS2 was transformed into PA340. The $P_{26}$ilvD gene was integrated into the original ilvD locus by homologous recombination. The resultant strain PA374 has the genotype $P_{26}$panBCD, $P_{26}$panE1, $P_{26}$ilvBNC, $P_{26}$ilvD, specR and trpC2 (Trp$^-$).

A pantothenic acid titer of up to 2.99 g/l (24 h) was achieved using the *Bacillus subtilis* strain PA374 in 10 ml cultures containing SVY medium which had been supplemented only with 5 g/l of β-alanine.

In order to produce pantothenic acid using strain PA374 without feed of β-alanine, additional copies of the gene panD coding for aspartate-α-decarboxylase were introduced into strain PA374. For this, chromosomal DNA of strain PA401 was transformed into PA374. Strain PA377 was obtained by selection on tetracycline.

The resultant strain PA377 has the genotype $P_{26}$panBCD, $P_{26}$panE1, $P_{26}$ilvBNC, $P_{26}$ilvD, specR, tetR and trpC2 (Trp$^-$).

A pantothenic acid titer of up to 1.31 g/l (24 h) was achieved without feed of precursors using *Bacillus subtilis* strain PA377 in 10 ml cultures containing SVY medium.

Preparation of *Bacillus subtilis* strain PA401 (genotype $P_{26}$panD) is described in the following section:

The *Bacillus subtilis* panD gene was cloned from the panBCD operon into a vector which carries the tetracycline marker gene. The promoter $P_{26}$ and an above-described artificial RBS were cloned in front of the panD gene. Restriction digestion produced a fragment which contained the tetracycline marker gene and the $P_{26}$panD gene. This fragment was religated and transformed into the above-described strain PA221. The fragment integrated into the genome of strain PA211. The resultant strain PA401 has the genotype $P_{26}$panBCD, $P_{26}$panD, tetR and trpC2 (Trp$^-$).

A pantothenic acid titer of up to 0.3 g/l (24 h) was achieved using the *Bacillus subtilis* strain PA401 in 10 ml cultures containing SVY medium which had been supplemented with 5 g/l of α-ketoisovalerate. In 10 ml cultures containing SVY medium which had been supplemented with 5 g/l of D-pantoic acid and 10 g/l of L-aspartate, pantothenic acid titers of up to 2.2 g/l (24 h) were achieved.

Starting from strain PA377, a tryptophan-prototrophic strain was generated by transformation with chromosomal DNA from strain PY79. This strain PA824 has the genotype $P_{26}$panBCD, $P_{26}$panE1, $P_{26}$ilvBNC, $P_{26}$ilvD, specR, tetR and Trp$^+$.

A pantothenic acid titer of up to 4.9 g/l (48 h) without supply of precursors was achieved using *Bacillus subtilis* strain PA824 in 10 ml cultures in SVY medium (comparison PA377: up to 3.6 g/l in 48 h).

The preparation of PA668 is described in the following section:

The *Bacillus* panB gene was cloned from the wild type panBCD operon and inserted into a vector which, in addition to a chloramphenicol resistance gene, also contains *B. subtilis* sequences of the vpr locus.

The strong constitutive promoter $P_{26}$ was introduced before the 5' end of the panB gene. One fragment which contains the $P_{26}$panB gene, the marker gene for chloramphenicol resistance and also *Bacillus subtilis* vpr sequences was obtained by restriction digestion. The isolated fragment was religated and used to transform strain PA824. The resultant strain was termed PA668. The genotype of PA668 is: $P_{26}$panBCD, $P_{26}$panE1, $P_{26}$ilvBNC, $P_{26}$ilvD, $P_{26}$panB, specR, tetR, CmR and Trp$^+$.

Two colonies of PA668 were isolated and termed PA668-2A, and the other PA668-24.

Using *B. subtilis* strain PA668-2A pantothenic acid titers of 1.5 g/l are achieved in 48 h in 10 ml cultures in SVY medium without supply of precursors. In 10 ml cultures supplemented with 10 g/l of aspartate, titers up to 5 g/l are achieved.

Using *B. subtilis* strain PA668-24, pantothenic acid titers of 1.8 g/l are achieved in 48 h in 10 ml cultures in SVY medium without supply of precursors. In 10 ml cultures supplemented with 10 g/l of L-aspartate, titers up to 4.9 g/l are achieved.

The exact construction of the strain is to be taken from the annexes of the PCT/US application 0025993 and U.S. Ser. No. 60/262,995.

Using the above-described strain PA377, in glucose-limited fermentation in SVY medium (25 g/l of Difco Veal Infusion Broth, 5 g/l of Difco Yeast Extract, 5 g/l of tryptophan, 5 g/l of Na glutamate, 2 g/l of $(NH_4)_2SO_4$, 10 g/l of $KH_2PO_4$, 20 g/l of $K_2HPO_4$, 0.1 g/l of $CaCl_2$, 1 g/l $MgSO_4$, 1 g/l of sodium citrate, 0.01 g/l of $FeSO_4.7H_2O$ and 1 ml/l of a trace salt solution of the following composition: 0.15 g of $Na_2MoO_4.2H_2O$, 2.5 g of $H_3BO_3$, 0.7 g of $CoCl_2.6H_2O$, 0.25 g of $CuSO_4.5H_2O$, 1.6 g of $MnCl_2.4H_2O$, 0.3 g of $ZnSO_4.7H_2O$, made up to 1 l with water)) on a 10 l scale with continuous supply of a glucose solution, pantothenic acid concentrations in the fermentation broth of 18-19 g/l 122-25 g/l) are achieved in 36 h (48 h).

In the case of glucose-limited fermentation of PA824, the tryptophan-prototroph derivative of PA377, in yeast extract medium (10 g/l of Difco Yeast Extract, 5 g/l of Na glutamate, 8 g/l of $(NH_4)_2SO_4$, 10 g/l of $KH_2PO_4$, 20 g/l of $K_2HPO_4$, 0.1 g/l of $CaCl_2$, 1 g/l of $MgSO_4$, 1 g/l of sodium citrate, 0.01 g/l of $FeSO_4.7H_2O$ and 1 ml/l of the above-described trace salt solution) the following pantothenic acid concentrations in fermentation broths are achieved in 36 h, 48 h and 72 h: 20 g/l, 28 g/l and 36 g/l, on a 10 l scale with continuous supply of a glucose solution.

By means of further optimization of media, using strain PA824 in glucose-limited fermentation in a medium consisting of 10 g/l of Difco Yeast Extract, 10 g/l of NZ amine A (Quest International GmbH, Erftstadt), 10 g/l of Na glutamate, 4 g/l of $(NH_4)_2SO_4$, 10 g/l of $KH_2PO_4$, 20 g/l of $K_2HPO_4$, 0.1 g/l of $CaCl_2$, 1 g/l of $MgSO_4$, 1 g/l of sodium citrate, 0.01 g/l of $FeSO_4.7H_2O$ and 1 ml/l of the above-described trace salt solution, pantothenic acid concentrations of 37 g/l (48 g/l) are achieved in fermentation broths in 36 h (48 h) on a 10 l scale with continuous supply of a glucose solution.

Further increases in the pantothenic acid concentration in the fermentation broth are conceivable by further optimization of media, by increasing the fermentation time, by process and strain improvement and by combinations of the individual steps. Thus the above-described pantothenic acid concentrations are also achievable by fermentation of strains which are derivatives of the above-described PA824. Derivatives can be prepared by classical strain development and by further genetic engineering manipulations. By development of media, strain and fermentation process, the pantothenic acid titers in the fermentation broths can be increased to greater than 40, 45, 50, 55, 60, 65, 70, 75, 80, 85 and >90 g/l.

An essential advantage of the inventive process is that the fermentation is carried out in a culture medium which, apart from at least one carbon source and nitrogen source, contains no other precursors as starting compounds. That is to say the biosynthesis of D-pantothenic acid is independent of the supply of other precursors. For the purposes of the present invention, such precursors are substances such as β-alanine and/or L-aspartate and/or L-valine and/or α-ketoisovalerate and/or combinations thereof.

In a preferred variant of the inventive process, the fermentation of the D-pantothenic-acid-producing organism is carried out in a culture medium which contains a carbon source and a nitrogen source, but to which no free β-alanine and/or β-alanine salts is/are added or supplied in the course of the fermentation. That is to say for producing D-pantothenic acid in ranges of at least 10 g/l of culture medium, preferably at least 20 g/l, particularly preferably at least 40 g/l, very particularly preferably at least 60 g/l, and in particular at least 70 g/l, no supply of free β-alanine and/or β-alanine salts is required according to the invention.

Independence from feed of precursors is in particular an important economic advantage of the inventive process compared with known processes, since a multiplicity of precursors are very expensive.

However, the invention does not exclude addition of β-alanine and/or β-alanine salts, so that therefore the yield of D-pantothenic acid can be further increased by adding β-alanine and/or β-alanine salts. If it is assumed, for example, that all of the required precursors of pantothenic acid are present in a sufficient amount, only the activity of the panD gene limits a further increase in pantothenic acid production, then the yield of pantothenic acid can be increased, for example, by a further 50% by adding free β-alanine and/or β-alanine salts.

In an advantageous variant of the present invention, up to 20 g/l of free β-alanine and/or β-alanine salts can be added to the culture medium for additional increase in the pantothenic acid yield by more than 50%. Preference is given to adding about 15 g/l of free β-alanine and/or β-alanine salts to the culture medium.

Examples of carbon sources which are suitable according to the invention for use in a culture medium for fermenting the abovementioned organisms are sugars, such as starch hydrolysates (mono-, di-, oligosaccharides), preferably glucose or sucrose, and also beet or cane sugar molasses, proteins, protein hydrolysates, soybean meal, corn steep liquor, fats, free fatty acids, recirculated cells from previous fermentations or hydrolysates thereof, and also yeast extract. This listing is not limiting for the present invention.

In addition, the present process is advantageously distinguished in that the total sugar content is reduced to a minimum up to the end of fermentation, since this would otherwise make difficult later drying and/or formulation of the fermentation solution owing to sticking. This can be achieved according to the invention by continuing the fermentation for some further time after the carbon source is consumed (in the case of batch culture) or after the carbon feed (in the case of a process procedure in the fed-batch or repeated fed-batch mode) is interrupted and/or regulated in such a manner that the concentration of the carbon source is virtually zero (in the case of fed-batch, repeated fed-batch or continuous process procedure).

This is achieved according to the invention by the means that, after interrupting the addition of the carbon source (for example sugar solution), the fermentation is continued until the dissolved oxygen concentration ($pO_2$) of at least 80%, preferably 90%, and particularly preferably 95%, of the saturation value is achieved in the fermentation solution.

Examples of nitrogen sources which are suitable according to the invention are ammonia, ammonium sulfate, urea, proteins, protein hydrolysates or yeast extract. This listing also is not limiting for the present invention.

In addition, the fermentation medium contains mineral salts and/or trace elements, such as amino acids and vitamins. The exact compositions of suitable fermentation media are known in abundance and accessible to those skilled in the art.

After the fermentation medium has been inoculated with a suitable D-pantothenic-acid-producing organism (at the cell densities known to those skilled in the art), if appropriate with addition of an antifoam, the organism is cultured. Any necessary regulation of the pH of the medium can be achieved using various inorganic or organic alkalis or acids, for example NaOH, KOH, ammonia, phosphoric acid, sulfuric acid, hydrochloric acid, formic acid, succinic acid, citric acid or the like.

On account of the buffer systems used during fermentation, which, as described above, can be, for example, NaOH, KOH, ammonia, phosphoric acid, sulfuric acid, hydrochloric acid, formic acid, succinic acid, citric acid or the like, the D-pantothenic acid formed is present in the fermentation solution, depending on the buffer system used, in the form of the respective salt(s). Since this in this case, in particular, the salts of D-pantothenic acid in the form of their monovalent cations are disadvantageous, the fermentation solution is prepared according to the invention with the use of a cation exchanger.

The present invention comprises here all commercially available cation exchangers. Cation exchangers suitable according to the invention for desalting pantothenate salts to give pantothenic acid are acid resins present in the $H^+$ form, acrylate-based having carboxylic functionalities and/or polystyrene resins having sulfonate groups, for example Lewatit CNP 80, CNP LF, S 100, S1468 and SP 112 Monopulus (Bayer, Leverkusen, Germany), Diaion PK 216 (Mitsubishi Chemical Corp, Tokyo, Japan), Amberlite 200 and Amberlite 252 (Rohm and Haas, Philadelphia, USA).

Preferred cation exchangers are strongly acidic ion exchangers in the $H^+$ form based on sulfonated polystyrene. Particular preference is given to monodisperse cation exchangers, for example Lewatit S1468. The preceding listing of cation exchangers is by way of example and not limiting for the present invention. As familiar to those skilled in the art, the ion exchangers, after exhaustion, can be regenerated back to the $H^+$ form using mineral acids, and thus can be used many times.

Using the cation exchanger removes the monovalent cations, for example ammonia, potassium or sodium, advantageously virtually completely from the fermentation solution, so that in the solution free D-pantothenic acid is formed from the D-pantothenic acid salts. According to the invention, the content of monovalent cations, preferably ammonium, potassium and/or sodium ions, is decreased to a concentration of $\leq 1$ g/kg of solution.

The resultant solution of free pantothenic acid is according to the invention set to a pH of 3-10 by adding calcium base and/or magnesium base. A pH of 5-10 is advantageous. Preferably, the solution is set to a pH of 5-9, particularly preferably 6-9, and very particularly preferably 6-8. In this manner a solution or suspension of calcium pantothenate and/or magnesium pantothenate is obtained. Preferably, for neutralization, calcium hydroxide, calcium carbonate, calcium oxide, magnesium hydroxide and/or basic magnesium carbonate is added to the solution in the form of a solid and/or as aqueous suspension.

It is preferred according to the invention in this case if the free D-pantothenic-acid-containing solution is neutralized with a calcium base and/or magnesium base in the form of an aqueous suspension. As a result of using an aqueous suspension the neutralization is performed more rapidly and without relatively large pH fluctuations than is the case when a corresponding solid is used.

According to the invention the process is distinguished in that an aqueous suspension comprising 2-55% by weight, preferably 10-50% by weight, and particularly preferably 20-40% by weight, of calcium hydroxide is added to the solution in step c). The invention additionally comprises a process in which an aqueous suspension comprising 2-65% by weight, preferably 10-50% by weight, and particularly preferably 20-40% by weight, of calcium carbonate is added to the solution in step c). In a further embodiment of the present invention, an aqueous suspension comprising 2-60% by weight, preferably 10-50% by weight, and particularly preferably 20-40% by weight, of magnesium hydroxide is added to the solution in step c) of the inventive process. The invention also comprises a process in which an aqueous suspension comprising 2-25% by weight, preferably 10-20% by weight, of basic magnesium carbonate is added to the solution in step c).

In a further variant, an acidic inorganic and/or organic calcium salt and/or magnesium salt can be added to the free D-pantothenic acid-containing solution from step b) in a subsequent step c), a solution or suspension being obtained which contains calcium pantothenate and/or magnesium pantothenate.

Advantageously, for the purposes of the present invention, acidic inorganic calcium salts and/or magnesium salts are the corresponding calcium and/or magnesium halides. Preferably, according to the invention, these are $CaCl_2$ and/or $MgCl_2$. For the purposes of the present invention, the acidic organic calcium salts and/or magnesium salts are, for example, highly water-soluble salts of organic anions. Preferably, these are, for example, calcium and/or magnesium formate, acetate, propionate, glycinate and/or lactate.

In the subsequent step d) the solution or suspension of calcium pantothenate and/or magnesium pantothenate is then subjected to a drying and/or formulation.

The resultant calcium- and/or magnesium-D-pantothenate-containing solution or suspension is dried and/or formulated using processes known per se, for example spray drying, spray granulation, fluidized-bed drying, fluidized-bed granulation, drum drying or spin-flash drying (Ullmann's Encyclopedia of Industrial Chemistry, 6$^{th}$ edition, 1999, electronic release, chapter "Drying of Solid Materials"). The gas inlet temperature in convection drying is in the range 100-280° C., preferably 120-210° C. The gas outlet temperature is 50-180° C., preferably 60-150° C. To establish a desired particle size distribution and the associated product properties, fine particles can be separated off and recirculated. In addition, course material can be ground in a mill and likewise then recirculated.

According to the invention, in the process described above, the reduction of complex workup steps is advantageous, in particular the avoidance of the use of organic solvents, with simultaneous production of a desired product having high biological value. In addition, according to the invention the amount of waste water produced is significantly reduced. This thus results in further savings in complex work up and disposal plants. Thus the inventive process is advantageously distinguished in that it is simpler, less susceptible to faults, less time-consuming, markedly less expensive and thus more economical than conventional processes.

However, this does not exclude the inventive process from being able to be varied. The inventive process steps a) to d) mentioned at the outset can be supplemented by one or more of the following process steps which are themselves familiar to those skilled in the art. In this case, all conceivable combinations of the additional (operational) process steps with the (essential) process steps a) to d) are covered by the invention.

Thus the solutions or suspensions resulting from the process steps a)-c) can be disinfected, for example by heating (sterilization) or other methods, for example pasteurization or sterile filtration.

In other variants of the inventive process, before the drying and/or formulation of the solution or suspension, at least one of and/or combinations of the following steps can be carried out, comprising lysis and/or sterilizing the biomass and/or separating off the biomass from the fermentation solution and/or adding further additives and/or concentrating the fermentation solution, preferably by removing water.

The present invention thus also relates to a process in which the lysis and/or sterilization of the biomass is carried out still in the fermentation solution or not until after the biomass is separated off from the fermentation solution. This can be performed, for example, by a temperature treatment, preferably at 80-200° C., and/or an acid treatment, preferably with sulfuric acid or hydrochloric acid, and/or enzymatically, preferably with lysozyme.

In a further embodiment of the present invention, the cells of the fermented microorganisms can be removed by filtration, separation (for example centrifugation) and/or decantation from the solutions or suspensions of the steps a), b) or c) of the inventive process. It is also conceivable that the solutions or suspensions of the steps a), b) or c) can be passed directly through a cation exchanger without separating off the organisms present. If the biomass is not separated off before the workup step via cation exchangers (step b)) of the inventive process, the biomass-containing fermentation solution can also advantageously be passed through the ion-exchange bed from bottom to top, that is to say in the opposite direction to gravity. This procedure is generally advantageous when suspended matter is present in the solution to be purified.

The solution or suspension resulting from the work up via the cation exchanger can, following neutralization, be concentrated via a suitable evaporator, for example falling-film evaporator, thin-film evaporator or rotary evaporator. In a further variant, the actual drying and/or formulation of the solution or suspension in step d) of the abovementioned inventive process can be preceded by concentration. For this the solution or suspension from step c) is concentrated, for example, in a falling-film evaporator and/or a thin-film evaporator. Such evaporators are manufactured, for example, by the companies GIG (4800 Attnang Puchheim, Austria), GEA Canzier (52303 Düren, Germany), Diessel (31103 Hildesheim, Germany) and Pitton (35274 Kirchhain, Germany).

To improve the color properties of the end product, an additional filtration step can be carried out in which a little activated carbon is added to the solutions or suspensions obtained during the process and the activated-carbon-containing suspension is then filtered. Or, the solutions obtained during the fermentation can be passed through a small activated carbon bed. The amounts of activated carbon used which are required for this are in the range of a few % by weight of the fermentation solution and are within the knowledge and experience of those skilled in the art.

These filtrations can be simplified by adding a commercial flocculating aid to the respective solution before filtration (for example Sedipur CF 902 or Sedipur CL 930 from BASF AG, Ludwigshafen).

In an advantageous embodiment of the present invention, the fermentation output (fermentation broth) is sterilized by heating and is then freed from the cell mass by centrifugation, filtration or decantation. After addition of 50-1000 mg/kg, preferably 100-200 mg/kg, of a commercially conventional flocculating aid, based on the fermentation output, the mixture is filtered through a short bed of activated carbon and sand in order to obtain a biomass-free solution having a high D-pantothenic acid content. This treated solution is then passed through the ion-exchange bed (in H$^+$ form).

If the biomass is not separated off before the inventive workup step via a cation exchanger, the biomass-containing fermentation solution advantageously can also be passed through the ion-exchange bed from bottom to top, that is to say in the opposite direction to gravity.

The solution or suspension containing calcium pantothenate and/or magnesium pantothenate can be then be dried, for example by spray drying. This can be performed in cocurrent, countercurrent or mixed flow.

For the atomization, all known atomizers can be used, in particular centrifugal atomizers (atomizer disk), single-fluid nozzle or two-fluid nozzle. Preferred drying temperature conditions are 150-250° C. tower inlet temperature and 70-130° C. tower exit temperature. However, drying can also be performed at higher or lower temperature levels. To achieve a very low residual moisture, a further drying step can be provided downstream in a fluidized bed.

The spray drying may also be carried out in an FSD or SBD dryer (FSD: fluidized spray dryer; SBD: spray bed dryer), as are manufactured by the companies Niro (Copenhagen, Denmark) and APV-Anhydro (Copenhagen, Denmark), which are a combination of spray dryer and fluidized bed.

In the spray drying an anticaking agent can be added. This can reduce the deposition on the dryer wall and improve the flow behavior, precisely in the case of fine-grained powders. Anticaking agents which can be used are, in particular, silicates, stearates, phosphates and corn starch.

In principle the drying can also take place in a sprayed fluidized bed, in which case this can be operated not only continuously but also batchwise. The solution or suspension can be sprayed in not only from the top (top spray) and from the bottom (bottom spray) but also from the side (side spray).

The present invention further relates to a composition for use as animal feed additive and/or animal feed supplement, in which case it can be prepared by a) using at least one organism which produces D-pantothenic acid and in which the biosynthesis of pantothenic acid (pan) and/or isoleucine/valine (ilv) is deregulated and which forms at least 2 g/l of salts of D-pantothenic acid by fermentation in a culture medium, 0-20 g/l, preferably 0 g/l, of free β-alanine and/or β-alanine salt being supplied to the culture medium, b) passing the D-pantothenate-containing fermentation solution through a cation exchanger, free D-pantothenic acid being formed from the salts of D-pantothenic acid, c) adding a calcium base and/or magnesium base to set the free D-pantothenic acid-containing solution to a pH of 3-10, a solution being obtained which contains calcium and/or magnesium pantothenate acid and d) subjecting the calcium pantothenate- and/or magnesium pantothenate-containing solution to drying and/or formulation.

In an advantageous variant, in step c) or step d), a suspension is obtained or charged which contains calcium pantothenate and/or magnesium pantothenate.

In a further variant, an acidic inorganic and/or organic calcium salt and/or magnesium salt can be added to the free D-pantothenic acid-containing solution from step b) in a following step c), a solution or suspension being obtained which contains calcium pantothenate and/or magnesium pantothenate.

Advantageously, for the purposes of the present invention, acidic inorganic calcium salts and/or magnesium salts are the corresponding calcium and/or magnesium halides. According to the invention these are preferably $CaCl_2$ and/or $MgCl_2$. Among the acidic organic calcium salts and/or magnesium salts, for the purposes of the present invention, are, for example, readily water-soluble salts of organic anions. Preferably these are, for example, calcium and/or magnesium formate, acetate, propionate, glycinate and/or lactate.

In the subsequent step d), the solution or suspension of the calcium pantothenate and/or magnesium pantothenate is subjected to a drying and/or formulation.

In addition the inventive composition is distinguished in that it comprises salts of D-pantothenic acid at a concentration of at least 1-100% by weight, preferably at least 20-100% by weight, and particularly preferably at least 50% by weight. The present invention relates to a composition which comprises salts of D-pantothenic acid in the form of divalent cations, preferably calcium and/or magnesium D-pantothenate. According to the invention preference is given to a composition which is distinguished in that the content of salts of D-pantothenic acid in the form of monovalent cations is $\leq 1$ g/kg.

According to the invention by means of the above-described process a calcium D-pantothenate or magnesium D-pantothenate is obtained which meets the requirements for a feed additive. These requirements are, for example, a relatively high content of D-pantothenate and a high compatibility with the target organism and biological value in the meaning of "vitamin activity" of the inventive product.

The present invention will be described in more detail by the following examples, which are not, however, limiting for the invention:

MODES FOR CARRYING OUT THE INVENTION

Example 1

In a laboratory fermenter containing stirrer and gas-introduction device of 14 l capacity, aqueous fermentation medium of the following composition is charged:

| Starting material | Concentration [g/l] |
| --- | --- |
| Yeast extract | 10 |
| Sodium glutamate | 5 |
| Ammonium sulfate | 8 |
| $KH_2PO_4$ | 6.7 |
| $K_2HPO_4$ | 9.8 |

After sterilization, the following sterile media components are additionally added:

| Starting material | Concentration [g/l] |
| --- | --- |
| Glucose | 2.5 |
| Calcium sulfate | 0.1 |
| Magnesium sulfate | 1 |
| Sodium citrate | 1 |
| $FeSO_4 \cdot 7H_2O$ | 0.01 |
| Trace salt solution | 1 ml |

The trace salt solution has the following composition:

0.15 g of $Na_2MoO_4 \cdot 2H_2O$, 2.5 g of $H_3BO_3$, 0.7 g of $CoCl_2 \cdot 6H_2O$, 0.25 g of $CuSO_4 \cdot 5H_2O$, 1.6 g of $MnCl_2 \cdot 4H_2O$, 0.3 g of $ZnSO_4 \cdot 7H_2O$ are made up to 1 l with water. The trace salt solution is added via sterile filtration. The initial liquid volume is 6 l. The contents set forth above are based on this value.

To this solution are added 60 ml of inoculation culture (OD=10) of *Bacillus subtilis* PA824 and the suspension is fermented at 43° C. with vigorous stirring at a gas introduction rate of 12 l/min. This strain is described in accordance with the annex in PCT/US Application 0025993.

Within the course of 47 h, 6.5 l of a sterile aqueous solution are added, the composition of which is as follows:

| Starting material | Concentration [g/l] |
|---|---|
| Glucose | 550 |
| Calcium sulphate | 0.7 |
| Trace salt solution | 6 ml |

The fermentation is carried out under glucose-limiting conditions. During the fermentation the pH is regulated to 7.2 by adding 25% strength ammonia solution or 20% strength phosphoric acid. Ammonia serves simultaneously as nitrogen source for the fermentation. The speed of rotation of the agitator element is controlled to keep the dissolved oxygen content to 30% of the saturation value. After halting the addition of the carbon source, the fermentation is continued until the dissolved oxygen content ($pO_2$) has reached a value of 95% of the saturation value. The fermentation is then ended and the organism is thermally destroyed. For this the fermentation solution is sterilized for 45 min. Successful destruction is demonstrating by plating out.

The cells are then separated off by centrifugation. After cell separation the concentration of D-pantothenate after 48 h is 22.8 g/l.

Similarly, fermentation broths may also be produced which have β-alanine-feed-free pantothenic acid titers of greater than 20, 25, 30, 35, 40, 45, 50, 55, 60, 65, 70, 75, 80, 85 and >90 g/l.

The fermentation output which is sterilized by heating as described above and has been substantially freed from the biomass by centrifugation is admixed with additional D-pantothenic acid and the pH is set to approximately 7 with 25% strength ammonium hydroxide solution (dispersion).

The resultant solution or suspension is filtered through a small bed of sand/activated carbon. The content of D-pantothenic acid in the filtrate is 70 g/l, the D-pantothenic acid principally being in the form of the ammonium salt.

1000 ml of this filtrate are passed by means of hydrostatic pressure through a 250 ml glass column in which glass column are situated approximately 100 ml of ion exchanger Lewatit S100 G1. The flow rate is controlled to approximately 20 ml/min.

100 ml fractions of the effluent were collected and analyzed for their pH, and the concentration of D-pantothenate and the ions $Ca^{2+}$, $Mg^{2+}$, $NH_4^+$, $K^+$ and $Na^+$. Fractions 1-3 are listed by way of example in the table below.

Example 2

In a laboratory fermenter containing stirrer and gas-introduction device of 14 l capacity, aqueous fermentation medium of the following composition is charged:

| Starting material | Concentration [g/l] |
|---|---|
| Yeast extract | 10 |
| Sodium glutamate | 5 |
| Ammonium sulfate | 8 |
| $KH_2PO_4$ | 8.4 |
| $K_2HPO_4$ | 15 |

After sterilization, the following sterile media components are additionally added:

| Starting material | Concentration [g/l] |
|---|---|
| Glucose | 2.5 |
| Calcium chloride | 0.1 |
| Magnesium chloride | 1 |
| Sodium citrate | 1 |
| $FeSO_4 \cdot 7H_2O$ | 0.01 |
| Trace salt solution | 1 ml |

The trace salt solution has the following composition:

0.15 g of $Na_2MoO_4.2H_2O$, 2.5 g of $H_3BO_3$, 0.7 g of $CoCl_2.6H_2O$, 0.25 g of $CuSO_4.5H_2O$, 1.6 g of $MnCl_2.4H_2O$, 0.3 g of $ZnSO_4.7H_2O$ are made up to 1 l with water. The trace salt solution is added via sterile filtration. The initial liquid volume is 5.5 l. The contents set forth above are based on this value.

To this solution are added 55 ml of inoculation culture (OD=10) of *Bacillus subtilis* PA824 and the suspension is fermented at 43° C. with vigorous stirring at a gas introduction rate of 12 l/min. This strain is described in accordance with the annex in PCT/US Application 0025993.

Within the course of 48 h, 6 l of a sterile aqueous solution are added, the composition of which is as follows:

| Sample | in ml | pH start | pH end | Pantothenate (g/l) | $NH_4^+$ | $CA^{2+}$ | $K^+$ | Ngphu 2+ | $Na^{30}$ |
|---|---|---|---|---|---|---|---|---|---|
| Filtrate | | | 7 | 70 | 0.76% | 0.11% | 0.20% | 0.003% | 0.031% |
| Fraction 1 | 100 | 4.5 | 1.5 | 1.2 | <1 ppm | <0.001% | <0.001% | <0.001% | 0.001% |
| Fraction 2 | 100 | 1.5 | 1.6 | 64 | 4 ppm | <0.001% | <0.001% | <0.001% | 0.003% |
| Fraction 3 | 100 | 1.6 | 2.5 | 68 | 19 ppm | 0.001% | <0.001% | <0.001% | 0.002% |

75 ml of Fraction 2 which contains 4.8 g of pantothenate were brought to a pH of 7, with stirring, by adding solid calcium hydroxide. The resultant calcium D-pantothenate solution or suspension was then dried by evaporating off water on a rotary evaporator and 8.98 g of a light-brown calcium D-pantothenate powder were obtained which has a content of 57% calcium D-pantothenate. This powder has no tendency to stick together and has good product properties.

| Starting material | Concentration [g/l] |
|---|---|
| Glucose | 550 |
| Calcium chloride | 0.6 |
| Trace salt solution | 6 ml |

The fermentation is carried out under glucose-limiting conditions. During the fermentation the pH was regulated to about 7.2 by adding 25% strength ammonia solution or 20% strength phosphoric acid. Ammonia serves simultaneously as nitrogen source for the fermentation. The speed of rotation of the agitator element is controlled to keep the dissolved oxygen content to 30% of the saturation value. After halting the addition of the carbon source, the fermentation is continued until the dissolved oxygen content ($pO_2$) has reached a value of 95% of the saturation value. The fermentation is then ended and the organism is thermally destroyed. For this the fermentation solution is sterilized for 30 min. Successful destruction is demonstrating by plating out.

The cells are then separated off by centrifugation. After cell separation the concentration of D-pantothenate on stopping after 48 h is 24.1 g/l. Similarly, fermentation broths may also be produced which have β-alanine-feed-free pantothenic acid titers of greater than 20, 25, 30, 35, 40, 45, 50, 55, 60, 65, 70, 75, 80, 85 and >90 g/l.

Of the fermenter output, 2817 ml are admixed with 1183 ml of a pantothenic acid solution of concentration 178.9 g/l and neutralized with 25% strength ammonia solution. The mixture is then filtered through sand/activated carbon. The content of D-pantothenic acid in the filtrate is 67 g/l, the D-pantothenic acid being present principally in the form of the ammonium salt.

1300 ml of the filtrate were transported through a bed (volume about 1 liter) of the ion exchanger Lewatit S100 G1 (in the $H^+$ form) and washed out with water. The flow rate is regulated to approximately 20 ml/min.

After a first running of 200 ml, 1810 g of the eluate were collected. The content of D-pantothenic acid was 45 g/l. The following ion concentrations are present: $NH_4^+$:66 mg/kg of eluate and $K^+$:<0.001 g/100 g of eluate. The phosphorus content is 0.072 g/100 g of eluate.

The free pantothenic acid is neutralized with solid calcium hydroxide with stirring, that is to say a pH of approximately 7 is set.

1840 g of an aqueous calcium D-pantothenate solution or suspension were obtained having a content of D-calcium pantothenate of 49 g/l.

This aqueous calcium D-pantothenate solution or suspension is dried in a Niro Minor laboratory spray-dryer. The inlet temperature is about 200° C. The outlet temperature is 85-90° C. The atomization is performed using a two-fluid nozzle at a pressure of 4 bar. The water content was carried out by the Karl-Fischer method. The pulverulent product has the following specification (data in % by weight):

Water content: 2%

Calcium D-pantothenate: 56.3%

Ammonium ions: 0.049%

Potassium ions: <0.01%

Sodium ions: <0.01%.

Example 3

In a laboratory fermenter containing stirrer and gas-introduction device of 300 l capacity, aqueous fermentation medium of the following composition is charged:

| Starting material | Concentration [g/l] |
| --- | --- |
| Soybean meal | 40 |
| Yeast extract | 5 |
| Sodium glutamate | 5 |
| Ammonium sulfate | 8 |
| $KH_2PO_4$ | 10 |
| $K_2HPO_4$ | 20 |

After sterilization, the following sterile media components are additionally added:

| Starting material | Concentration [g/l] |
| --- | --- |
| Glucose | 2.5 |
| Calcium sulfate | 0.1 |
| Magnesium sulfate | 1 |
| Sodium citrate | 1 |
| $FeSO_4 \cdot 7H_2O$ | 0.01 |
| Trace salt solution | 1 ml |

The trace salt solution has the following composition: 0.15 g of $Na_2MoO_4 \cdot 2H_2O$, 2.5 g of $H_3BO_3$, 0.7 g of $CoCl_2 \cdot 6H_2O$, 0.25 g of $CuSO_4 \cdot 5H_2O$, 1.6 g of $MnCl_2 \cdot 4H_2O$, 0.3 g of $ZnSO_4 \cdot 7H_2O$ are made up to 1 l with water. The trace salt solution is added via sterile filtration. The initial liquid volume is 100 l. The contents set forth above are based on this value.

To this solution are added 4 l of inoculation culture (OD=120) of *Bacillus subtilis* PA824 and the suspension is fermented at 43° C. with vigorous stirring at a gas introduction rate of 1.8 $m^3$/h. This strain is described in accordance with the annex in PCT/US Application 0025993.

Within the course of 43 h, 113 l of a sterile aqueous solution are added, the composition of which is as follows:

| Starting material | Concentration [g/l] |
| --- | --- |
| Glucose | 550 |
| Calcium chloride | 0.6 |
| Sodium citrate | 2 |
| $FeSO_4 \cdot 7H_2O$ | 0.02 |
| Sodium glutamate | 5 |
| Trace salt solution | 1 ml |

The fermentation is carried out under glucose-limiting conditions. During the fermentation the pH is regulated to 7.2 by adding 25% strength ammonia solution or 20% strength phosphoric acid. Ammonia acts simultaneously as nitrogen source for the fermentation. The speed of rotation of the agitator element is controlled to keep the dissolved oxygen content to 30% of the degree of saturation. After halting the addition of the carbon source, the fermentation is continued until the dissolved oxygen content ($pO_2$) has reached a value of 95% of the saturation value. After 43 h, the fermentation is ended. The cells are removed by separating in a disk centrifuge. The cell-free fermentation solution is then sterilized for 60 min. Successful destruction is demonstrated by plating out.

The concentration of D-pantothenate after cell separation and sterilization is 21 g/l.

Similarly, fermentation broths may also be produced which have β-alanine-feed-free pantothenic acid titers of greater than 20, 25, 30, 35, 40, 45, 50, 55, 60, 65, 70, 75, 80, 85 and >90 g/l.

3270 ml of the resultant fermentation output are then fortified with 1750 ml of sodium pantothenate solution of a concentration of 170 g/l. Approximately 7 g of powdered activated carbon are then stirred into this solution. To improve the filterability of the suspension, one half of this is admixed with Sedipur CF 902 (48 g of a 1% strength solution) and the other half admixed with Sedipur CL 930 (30 g of a 1% strength solution). After being briefly stirred up, both halves are each filtered through a small celite bed and then recombined.

Of the resultant filtrate having a D-pantothenic acid content of 65.4 g/l, 1800 ml are passed through a bed (volume 1 liter) of the ion exchanger Lewatit S100 G1 (in the $H^+$ form) and washed out with water. The flow rate is approximately 20 ml/min.

After a first running of 250 ml, which is discarded, 2.2 l of the eluate are collected and the pH is set to approximately 7 by adding an aqueous 20% strength calcium hydroxide dispersion (milk of lime). The eluate is filtered again through a paper filter and, as filtrate, 2174 g of an aqueous calcium D-pantothenate solution or suspension having a content of 58 g/l calcium D-pantothenate is obtained after sample removal.

The subsequent spray drying is performed in a Niro Minor laboratory spray dryer. The inlet temperature is about 185° C., the outlet temperature approximately 95° C. The atomization is performed using a two-fluid nozzle at a pressure of 2 bar. The water content was carried out by the Karl-Fischer method. The resultant pulverulent product has the following specification (data in % by weight):

Water content: 1.4%

Calcium D-pantothenate: 63.2%

Ammonium ions: 0.043%

Potassium ions: <0.01%

Sodium ions: <0.01%

Example 4

In a fermenter equipped with stirrer and gas-introduction device of 20 l capacity, 200 g of soybean meal, 50 g of 50% strength yeast extract, 25 g of Na glutamate, 40 g of ammonium sulfate and 5 ml of antifoam agent Tego KS911 were admixed with 3.9 l of deionized water and the contents were sterilized at 121° C. for 30 min.

Solutions 1, 2, 3 and 4 were then added.

Solution 1 was made up as follows: 12.5 g of glucose, 0.5 g of $CaCl_2.2H_2O$ and 5 g of $MgCl_2.6H_2O$ were dissolved in 100 ml of deionized water and sterile-filtered.

Solution 2 was made up as follows: 25 ml of citrate-iron solution (200 g/l of sodium citrate, 2 g/l of $FeSO_4.7H_2O$, sterile-filtered) were admixed with 5 ml of trace salt solution (0.15 g of $Na_2MoO_4.2H_2O$, 2.5 g of $H_3BO_3$, 0.7 g of $CoCl_2.6H_2O$, 0.25 g of $CuSO_4.5H_2O$, 1.6 g of $MnCl_2.4H_2O$, 0.3 g of $ZnSO_4.7H_2O$ were made up to 1 l with water, sterile-filtered).

Solution 3 was made up as follows: 87.5 g of glucose were made up to 500 ml with water and sterilized.

Solution 4 was made up as follows: 25 g of $KH_2PO_4$, 50 g of $K_2HPO_4$, 25 g of $NaH_2PO_4$ and 50 g of $Na_2HPO_4$ were made up to 500 ml with water and sterilized.

To the mixed medium (volume after addition of all solutions: 5l) were added 100 ml of inoculation culture (OD=9.5 in SVY medium (SVY medium: Difco Veal Infusion broth 25 g, Difco Yeast extract 5 g, sodium glutamate 5 g, $(NH_4)_2SO_4$ 2.7 g in 740 ml of $H_2O$, sterilize; add 200 ml of sterile 1M $K_2HPO_4$ (pH 7) and 60 ml of sterile 50% glucose solution (final volume 1 L))) of *Bacillus subtilis* PA668-2A and the culture was fermented at 43° C. with vigorous stirring at a gas-introduction rate of 12 l/min. This strain is described according to the annex in U.S. Application Ser. No. 60/262,995.

In the course of 48 h, approximately 3.5 l of a sterile aqueous glucose solution were added. The solution was made up as follows: 5 kg of glucose.$H_2O$ and 3.6 g of $CaCl_2.2H_2O$ were admixed with 1.2 kg of deionized water and sterilized for 30 min. Then, 9 ml of trace salt solution (for composition see above) and 37.5 ml of citrate-iron solution (for composition see above) were added. 60 ml of sterile-filtered 375 g/l sodium glutamate solution were then added.

The fermentation was carried out under glucose-limiting conditions. During the fermentation the pH was kept at 7.2 by adding 25% strength ammonia solution or 20% strength phosphoric acid. Ammonia acted simultaneously as nitrogen source for the fermentation. The speed of rotation of the agitator element was controlled to keep the dissolved oxygen content to 20% of the saturation value. The foaming was controlled by occasional adding of the antifoam Tego KS 911. After halting the addition of the carbon source, the fermentation was continued until the dissolved oxygen content ($pO_2$) had reached a value of 95% of the saturation value. The fermentation was then ended. The cells were separated off by centrifugation. Residual cells in the supernatant were destroyed thermally by sterilization. The destruction was demonstrated by plating out. After separation and sterilization, the D-pantothenate concentration was 35.8 g/l. Similarly, fermentation broths can also be produced which have β-alanine-feed-free pantothenic acid-titers greater than 15, 20, 25, 30, 35, 40, 45, 50, 55, 60, 65, 70, 75, 80, 85 and greater than 90 g/l.

Example 5

1000 ml of the centrifuged material from Example 4 were fortified with synthetic sodium pantothenate to 70 g/l and pumped from top to bottom through a 1000 ml glass column in which was situated approximately 1000 ml of ion-exchanger Lewatit S100 G1. The flow rate was controlled to approximately 20 ml/min.

250 ml fractions were collected from the effluent and analyzed with respect to their pH, D-pantothenate concentration and for the ions $Ca^{2+}$, $Mg^{2+}$, $NH_4^+$, $K^+$ and $Na^+$. Fractions 1-3 are listed in the table below by way of example.

| Sample | in ml | pH | Pantothenate (g/l) | $NH_4^{30}$ | $Ca^{2+}$ | $K^+$ | $Mg^{2+}$ | $Na^+$ |
|---|---|---|---|---|---|---|---|---|
| Filtrate | | 7 | 70 | 0.48% | 0.01% | 0.57% | 0.003% | 0.51% |
| Fraction 1 | 250 | 2.05 | 34.1 | <0.01% | <0.01% | 0.0005% | <0.01% | 0.0004% |

-continued

| Sample | in ml | pH | Pantothenate (g/l) | $NH_4^{30}$ | $Ca^{2+}$ | $K^+$ | $Mg^{2+}$ | $Na^+$ |
|---|---|---|---|---|---|---|---|---|
| Fraction 2 | 250 | 1.94 | 55.2 | <0.01% | <0.01% | 0.0005% | <0.01% | 0.0003% |
| Fraction 3 | 250 | 1.91 | 61.7 | <0.01% | <0.01% | 0.004% | <0.01% | <0.0003% |

250 ml of fraction 2 were brought to a pH of 7 by adding solid calcium hydroxide with stirring. A white precipitate was produced which was filtered off after adding Sedipur CF902. The filtrate was then dried by evaporating off the water on a rotary evaporator and 25 g of a light-brown calcium D-pantothenate powder were obtained which had a content of 55% pantothenate. This powder does not have a tendency to stick together and has good product properties.

Example 6

1000 ml of the fortified centrifuged material from Example 5 were pumped from bottom to top through a bed (volume about 1 liter) of the ion exchanger Lewatit S100 G1 (in the $H^+$ form). This was then washed through with water. The flow rate was controlled to approximately 20 ml/min.

After a first running of 500 ml, 1750 g of the eluate were collected. The D-pantothenate content was 35 g/l. The following ion concentrations were present in the eluate: $NH_4^+$, <0.01%, $Na^+$: 0.0064%, $K^+$: 0.006%, $PO_4^{3-}$: 0.29%, $SO_4^{2-}$: 0.1% and $Cl^-$: 0.043%.

The free pantothenic acid was neutralized with solid calcium hydroxide with stirring, that is to say a pH of approximately 7 was set.

Approximately 1800 g of an aqueous calcium D-pantothenate suspension having a pantothenate content of approximately 35 g/l were obtained.

This aqueous calcium D-pantothenate suspension was dried in a Niro Minor laboratory spray dryer. The inlet temperature was about 200° C., and the outlet temperature was 85-90° C. The atomization was performed using a two-fluid nozzle at a pressure of 4 bar. The water content was carried out by the Karl-Fischer method. The pulverulent product had the following specification (data in % by weight):

Water content: 2%

D-pantothenate: 56.3%

Ammonium ions: 0.03%

Potassium ions: <0.015%

Sodium ions: <0.019%

Calcium ions: 9.5%

Example 7

3270 ml of the fermentation output obtained in Example 4 were fortified with 1750 ml of sodium pantothenate solution of a concentration of 125.6 g/l of pantothenate. Then approximately 7 g of powdered activated carbon were stirred into this solution. To improve the filterability of the suspension, one half of this was admixed with Sedipur CF 902 (48 g of a 1% strength solution). After stirring them up briefly, both halves were each filtered through a small celite bed and then recombined.

Of the resulting filtrate having a D-pantothenic acid content of 66.5 g/l, 1000 ml were passed through a bed (volume 1 liter) of the ion exchanger Lewatit S100 G1 (in the $H^+$ form). It was washed out with water. The flow rate was approximately 20 ml/min.

After the first running of 500 ml which was discarded 2 l of the eluate were collected and the pH was set to approximately 7 by adding an aqueous 20% strength calcium hydroxide dispersion (milk of lime). The eluate was filtered once more through a paper filter and as filtrate approximately 1960 ml of an aqueous calcium D-pantothenate solution or suspension having a D-pantothenate content of 16 g/l were obtained after sampling.

The following spray drying was performed in Niro Minor laboratory spray dryer. The inlet temperature was about 185° C., the outlet temperature approximately 95° C. The atomization was performed by means of a two-fluid nozzle at a pressure of 2 bar. The water content was carried out by the Karl-Fischer method. The resultant pulverulent product had the following specification (data in % by weight):

Water content: 1.4%

D-Pantothenate: 51%

Ammonium ions: 0.01%

Potassium ions: 0.012%

Sodium ions: 0.01%

Calcium ions: 7.7%

Example 8

In a similar manner to Example 4, in a further fermentation using strain PA668-2A, a fermentation broth having a pantothenic acid concentration of 22 g/l was obtained.

1000 ml of the centrifuged material was fortified with sodium pantothenate to 70 g/l and passed through a bed (volume about 1 liter) of the ion exchanger Amberlite 200 (in the $H^+$ form) and washed out with water.

After a first running of 500 ml, 2000 ml of the eluate were collected. The D-pantothenic acid content was 32.6 g/l. The following ion concentrations were present in the eluate: $NH_4^+$: <0.01%, $Na^+$: 0.0062%, K+: 0.00045%, $PO_4^{3-}$: 0.06%, $SO_4^{2-}$: 0.06% and $Cl^-$: 0.02%. The ion-exchange column, for regeneration, was first flushed with 1000 ml of 1N sodium hydroxide solution and 2500 ml of water. The ion exchanger was then regenerated with 1000 ml of 10% strength hydrochloric acid and the column was then washed to neutrality with 2500 ml of water.

The free pantothenic acid was neutralized with solid calcium hydroxide with stirring, that is to say a pH of about 7 was set.

Approximately 2000 g of an aqueous calcium D-pantothenate suspension having a pantothenate content of 27.35 g/l were obtained.

This aqueous calcium D-pantothenate suspension was dried in a Niro Minor laboratory spray dryer. The inlet temperature was about 200° C., and the outlet temperature 85-90° C. The atomization was performed by means of a two-fluid nozzle at a pressure of 4 bar. The water content was carried out by the Karl-Fischer method. The pulverulent product had the following specification (data in % by weight):

Water content: 1.7%

D-Pantothenate: 64.6%

Ammonium ions: 0.08%

Potassium ions: 0.006%

Sodium ions: 0.086%

Calcium ions: 6.5%

Example 9

In a similar manner to Example 4, a fermentation broth was obtained in a 40-hour fermentation using strain PA668-2A. This was freed from biomass by centrifugation and had a pantothenic acid concentration of 42.9 g/l. 1000 ml of this unsterilized fermenter broth was passed through a bed (volume about 1.0 liter) of the ion exchanger S1468 (in the $H^+$ form) and washed out with water. The flow rate was regulated to approximately 20 ml/min.

After a first running of 500 ml, 2100 ml of the eluate were collected. The D-pantothenic acid content was 19.2 g/l. The ion-exchange column, for regeneration, was first flushed with 1000 ml of 1N sodium hydroxide solution and 2500 ml of water. The ion exchanger was then regenerated with 1000 ml of 10% strength hydrochloric acid and the column was then washed to neutrality with 2500 ml of water.

The free pantothenic acid was neutralized with solid calcium hydroxide with stirring, that is to say a pH of approximately 7 was set. Approximately 2000 g of an aqueous calcium D-pantothenate suspension were obtained, which suspension was sterilized for 60 min. Successful destruction was demonstrated by plating out.

This aqueous calcium D-pantothenate suspension was dried in a Niro Minor laboratory spray dryer. The inlet temperature was about 200° C. and the outlet temperature 85-90° C. The atomization was performed by means of a two-fluid nozzle at a pressure of 4 bar. The water content was carried out by the Karl-Fischer method. The pulverulent product had the following specification (data in % by weight):

Water content: 2.6%

D-Pantothenate: 8.5%

Ammonium ions: <0.01%

Potassium ions: 0.003%

Sodium ions: 0.016%

Calcium ions: 0.61%

Example 10

To 2305 ml of the centrifuged material obtained from Example 4 having a D-pantothenic acid content of 35.8 g/l were added 895 ml of sodium pantothenate solution having a pantothenate content of 158.6 g/l. 1000 ml of this broth was passed through a bed (volume 1 liter) of the ion exchanger Lewatit S100 G1 (in the $H^+$ form) and washed out with water. The flow rate was approximately 20 ml/min.

After the first running of 500 ml which was discarded, 2 l of the eluate were collected. The D-pantothenate content of the eluate was 25.3 g/l. 1 equivalent of calcium ions in the form of calcium chloride, based on pantothenic acid, was added.

The following spray drying was performed in a Niro Minor laboratory spray dryer. The inlet temperature was about 185° C., and the outlet temperature approximately 95° C. The atomization was performed by means of a two-fluid nozzle at a pressure of 2 bar. The water content was carried out by the Karl-Fischer method. The resultant pulverulent product had the following specification (data in % by weight):

Water content: 2.1%

D-Pantothenate: 50%

Ammonium ions: <0.01%

Potassium ions: 0.015%

Sodium ions: <0.01%

Calcium ions: 8.0%

We claim:

1. A process for preparing D-pantothenic acid and/or salts thereof which comprises
    a) fermenting at least one bacterium from the Bacillaceae family which produces D-pantothenic acid and in which the biosynthesis of pantothenic acid (pan) and/or isoleucine/valine (ilv) is deregulated and which forms at least 2 g/L of salts of D-pantothenic acid by fermentation in a culture medium, wherein no free β-alanine and/or β-alanine salt is fed to the culture medium,
    b) passing the D-pantothenate-containing fermentation solution through a cation exchanger, free D-pantothenic acid being formed from the salts of D-pantothenic acid, wherein the content of monovalent cations is reduced,
    c) adding a calcium base or salt and/or magnesium base or salt to set the free D-pantothenic acid-containing solution to a pH of 3-10, a solution or suspension being obtained which contains calcium and/or magnesium pantothenate and
    d) subjecting the calcium pantothenate- and/or magnesium pantothenate-containing solution to drying and/or formulation.

2. The process as claimed in claim 1, wherein the bacterium is of the genus *Bacillus*.

3. The process as claimed in claim 1, wherein, in step a) a content of D-pantothenic acid and/or salts thereof of at least 10 g/l of culture medium is formed.

4. The process as claimed in claim 1, wherein, in step b), the content of monovalent cations is reduced to a concentration of ≦1 g/kg of solution.

5. The process as claimed in claim 1, wherein, in step c), the pH of the solution is set to 5-10.

6. The process as claimed in claim 1, wherein, in step c), the pH of the solution is set to 6-8.

7. The process as claimed in claim 1, wherein, for neutralization, calcium hydroxide, calcium carbonate, calcium oxide, magnesium hydroxide and basic magnesium carbonate is added in the form of a solid and/or as aqueous suspension to the solution in step c).

8. The process as claimed in claim 1, wherein an aqueous suspension comprising 2-55% by weight of calcium hydroxide is added to the solution in step c).

9. The A process as claimed in claim 1, wherein an aqueous suspension comprising 2-65% by weight of calcium carbonate is added to the solution in step c).

10. The process as claimed in claim 1, wherein an aqueous suspension comprising 20-60% by weight of magnesium hydroxide is added to the solution in step c).

11. The process as claimed in claim 1, wherein an aqueous suspension comprising 2-25% by weight of basic magnesium carbonate is added to the solution in step c).

12. The process as claimed in claim 1, wherein an inorganic and/or organic calcium salt and/or magnesium salt is added in step c) to the solution containing free D-pantothenic acid.

13. The process as claimed in claim 1, wherein, in step c), the calcium salt and/or magnesium salt is a corresponding halide.

14. The process as claimed in claim 1, wherein, in step c), the calcium salt and/or magnesium salt is $CaCl_2$ and/or $MgCl_2$.

15. The process as claimed in claim 12, wherein, in step c), the calcium salt and/or magnesium salt is calcium and/or magnesium formate, acetate, propionate, glycinate and/or lactate.

16. The process as claimed in claim 1, wherein a suspension which contains calcium pantothenate and/or magnesium pantothenate is obtained in step c), and a suspension which contains calcium pantothenate and/or magnesium pantothenate is employed in step d).

* * * * *